United States Patent
Todo et al.

(10) Patent No.: US 10,935,517 B2
(45) Date of Patent: Mar. 2, 2021

(54) GAS SENSOR ELEMENT AND GAS SENSOR UNIT

(71) Applicant: DENSO CORPORATION, Kariya (JP)

(72) Inventors: Yusuke Todo, Kariya (JP); Mitsunobu Nakato, Kariya (JP); Hiroaki Yoto, Kariya (JP)

(73) Assignee: DENSO CORPORATION, Kariya (JP)

(*) Notice: Subject to any disclaimer, the term of this patent is extended or adjusted under 35 U.S.C. 154(b) by 0 days.

(21) Appl. No.: 15/848,321

(22) Filed: Dec. 20, 2017

(65) Prior Publication Data

US 2018/0172626 A1 Jun. 21, 2018

(30) Foreign Application Priority Data

Dec. 20, 2016 (JP) .............................. JP2016-246584

(51) Int. Cl.
| | | |
|---|---|---|
| *G01N 27/419* | (2006.01) | |
| *G01N 27/407* | (2006.01) | |
| *G01N 27/409* | (2006.01) | |
| *G01N 27/41* | (2006.01) | |
| *G01N 33/00* | (2006.01) | |

(52) U.S. Cl.
CPC ......... *G01N 27/419* (2013.01); *G01N 27/409* (2013.01); *G01N 27/4071* (2013.01); *G01N 27/4074* (2013.01); *G01N 27/4075* (2013.01); *G01N 27/41* (2013.01); *G01N 33/0036* (2013.01)

(58) Field of Classification Search
CPC ....... G01N 27/404–407; G01N 27/409; G01N 27/419; G01N 27/41; G01N 27/4072; G01N 27/4067; G01N 27/4074; G01N 27/417
See application file for complete search history.

(56) References Cited

U.S. PATENT DOCUMENTS

| | | | | |
|---|---|---|---|---|
| 2006/0231397 A1* | 10/2006 | Nakagaki | ........... | G01N 27/4045 204/431 |
| 2013/0092537 A1* | 4/2013 | Mizutani | .............. | G01N 27/419 204/427 |
| 2015/0293051 A1* | 10/2015 | Kajiyama | .......... | G01N 27/4075 204/424 |
| 2016/0209354 A1 | 7/2016 | Araki et al. | | |
| 2016/0209358 A1 | 7/2016 | Toudou et al. | | |
| 2016/0320334 A1 | 11/2016 | Nakatou et al. | | |
| 2017/0191957 A1 | 7/2017 | Toudou et al. | | |

FOREIGN PATENT DOCUMENTS

| | | |
|---|---|---|
| JP | 2001-66289 | 3/2001 |
| JP | 2017-020838 | 1/2017 |

* cited by examiner

*Primary Examiner* — Gurpreet Kaur
(74) *Attorney, Agent, or Firm* — Nixon & Vanderhye P.C.

(57) ABSTRACT

A gas sensor element of the present disclosure includes a measurement gas chamber, a solid electrolyte body, and a sensor electrode. The sensor electrode has a noble metal region which contains at least Rh and Pt, an electrolyte region which is formed by a solid electrolyte, and a mixed region in which the noble metal and the solid electrolyte are mixed. With respect to a correlation curve which represents a correlation between a mass percentage concentration c of Rh and a thickness d of the mixed region, when a reaction resistance to a measured gas in the sensor electrode is 40 kΩ, the concentration c of Rh and the thickness d are set so that at coordinates (c, d), the concentration c has a positive coordinate point and the thickness d has a positive coordinate point.

12 Claims, 4 Drawing Sheets

Side View

GAS SENSOR ELEMENT AND GAS SENSOR UNIT

CROSS REFERENCE TO RELATED APPLICATIONS

This application is based on and claims the benefit of priority from Japanese Patent Application 2016-246584 filed on Dec. 20, 2016, the disclosures of which are incorporated in its entirety herein by reference.

BACKGROUND OF THE INVENTION

Technical Field

The present disclosure relates to a gas sensor element which detects a concentration of a specific gas in a measured gas and a gas sensor unit which is configured to include the gas sensor element.

Background Art

A gas sensor element which is configured to include a solid electrolyte body and an electrode provided on the solid electrolyte body and electrically detects a concentration of a specific gas in a measured gas by reducing the measured gas is known. In a gas sensor element disclosed in Patent Literature 1, a sensor electrode for detecting a specific gas has a noble metal region which is made of noble metal as a catalyst for reducing the specific gas, a solid electrolyte region which is made of a solid electrolyte contributing to ionic conduction, and further a mixed region in which the noble metal and the solid electrolyte are mixed.

In the mixed region, a three-phase interface of a noble metal portion, a solid electrolyte portion, and a vapor phase containing the specific gas is likely to occur. The three-phase interface is a reaction site where a reduction reaction to molecules in the measured gas occurs. By having the thicker mixed region, it is possible to decrease a reaction resistance for the reaction and a diffusion resistance for ion diffusion which occurs after the reduction. This enables improvement in reduction reactivity of the sensor electrode to the specific gas in the measured gas.

CITATION LIST

Patent Literature

[PTL 1] JP 2014-122878 A

SUMMARY

Technical Problem

The gas sensor element as described above is assumed to be exposed to a severe heating to and cooling environment, for example, by being mounted on a vehicle. In such an environment, a physical property of the mixed region may change so that the reaction resistance is increased. This may hinder the improvement in reduction reactivity to the specific gas achieved by expanding the thickness of the mixed region.

In view of the problem, an object of the present disclosure is to provide a gas sensor element and gas sensor unit which have high reduction reactivity while maintaining a thickness of a mixed region to be relatively small.

Solution to Problem

In order to achieve the object, a gas sensor element of the present disclosure includes: a measurement gas chamber into which a measured gas is introduced; a solid electrolyte body which is disposed in the measurement gas chamber and has oxygen ion conductivity; and a sensor electrode which is formed on a substrate constituted by the solid electrolyte body for detecting a concentration of a specific gas in the measured gas, the sensor electrode containing noble metal which contains at least rhodium and platinum, and a solid electrolyte which is identical in quality to the solid electrolyte body of the substrate and having a noble metal region which is formed by the noble metal, an electrolyte region which is formed by the solid electrolyte, and a mixed region in which the noble metal and the solid electrolyte are mixed, in a case where in a c-d orthogonal coordinate system which is defined by a mass percentage concentration c of rhodium to a total mass of platinum and rhodium in the noble metal and a thickness d of the mixed region, a correlation curve which represents a correlation between the concentration c and the thickness d when a reaction resistance to the measured gas is constant is defined, the correlation curve being a curve in which the thickness d of the mixed region asymptotically approaches zero as the mass percentage concentration c increases, and in the sensor electrode, the mass percentage concentration c of rhodium and the thickness d of the mixed region being set so that at coordinates (c, d) that is a combination of the concentration c and the thickness d, the concentration c has a positive coordinate point and the thickness d has a positive coordinate point with respect to the correlation curve when the reaction resistance is 40 kΩ.

A resistance for a reaction related to the detection of the concentration of the specific gas is a sum total of a diffusion/reaction resistance for a reduction reaction of molecules in the measured gas and ion diffusion after the reduction, a charge transfer resistance for ionic conduction in the electrolyte region in the sensor electrode, and an electrolyte resistance for ionic conduction of the solid electrolyte body which is the substrate. This total resistance is referred to as reaction resistance. Among these, the diffusion/reaction resistance and the charge transfer resistance are dominant in the resistance for the reaction related to the detection of the concentration of the specific gas.

According to the gas sensor element of the present disclosure, by appropriately setting the mass percentage concentration c of rhodium in the sensor electrode based on a correlation curve A, the reaction resistance of less than 40 kΩ is possible while maintaining the thickness d of the mixed region relatively small. That is, it is possible to improve reduction reactivity of the sensor electrode to the specific gas.

DETAILED DESCRIPTION OF THE PREFERRED EMBODIMENTS

The following describes embodiments of the present disclosure with reference to the drawings. In each of the embodiments, portions corresponding to matters described in a previous embodiment are given the same reference signs and duplicate descriptions may be omitted. In each of the embodiments, in a case where only a part of a configuration is described, another embodiment previously described is applicable to other parts of the configuration. Besides possible combinations of portions specifically and explicitly stated in each of the embodiments, partial combinations of the embodiments not explicitly stated are also possible if such combinations have no particular problem.

First Embodiment

Figure 1:
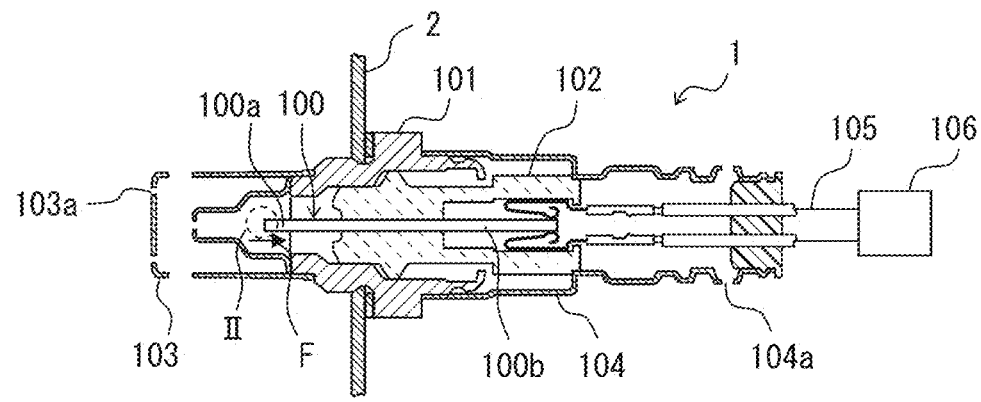
FIG. 1 is a side cross-sectional view showing a schematic structure of a gas sensor unit according to a first embodiment.
Figure 2:
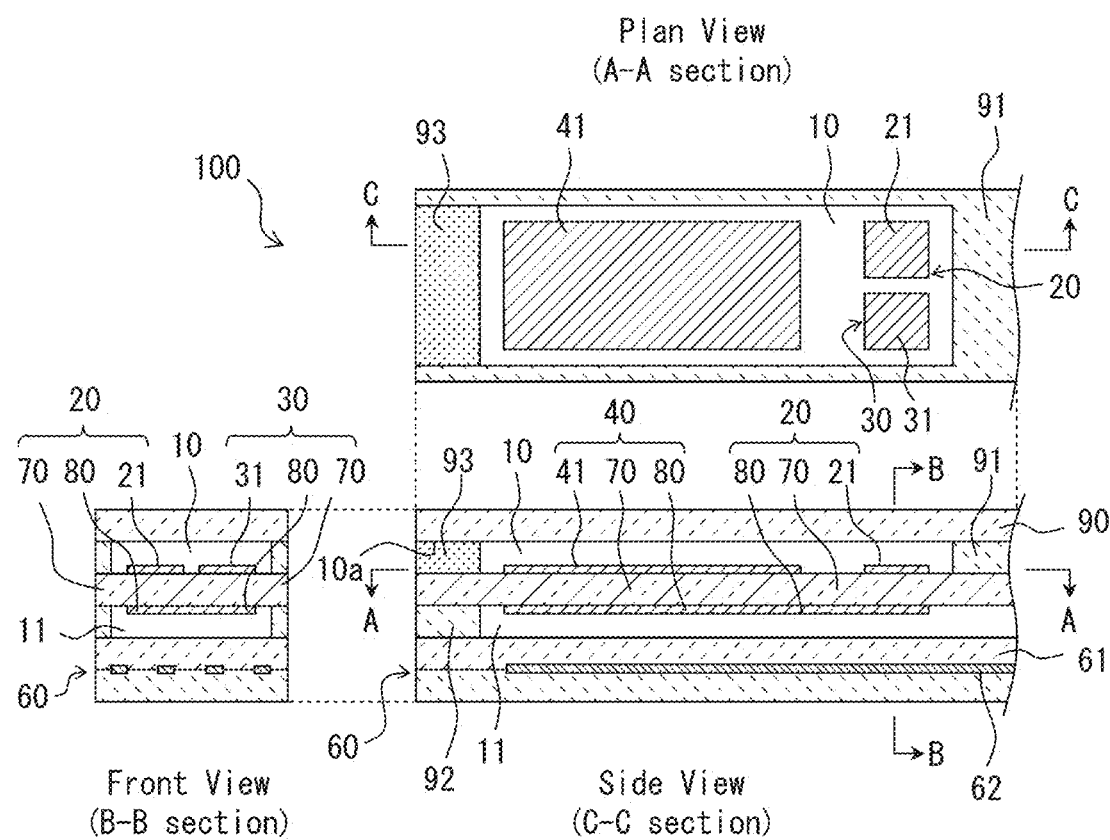
FIG. 2 is a cross-sectional view showing a detailed configuration of a gas sensor element.

First, the following describes, with reference to FIGS. 1 and 2, a schematic structure of a gas sensor element and a gas sensor unit according to the present embodiment.

The gas sensor element according to the present embodiment is, for example, a NOx sensor which detects an amount of nitrogen oxide (NOx). Such a gas sensor element is disposed and used, for example, in an exhaust pipe through which an exhaust gas flows in an internal combustion engine. A measured gas is the exhaust gas, and a specific gas whose concentration is to be detected is NOx.

The gas sensor unit is a module including the gas sensor element. For example, in the exhaust pipe, the gas sensor unit is mounted as a unit.

The following description is based on the premise that the specific gas in the measured gas is NOx. Note, however, that the specific gas to be detected is not limited to NOx, and the gas sensor element can be implemented as a sensor which detects, for example, ammonia or other kinds of gas, depending on constituent materials of a solid electrolyte body and an electrode.

As shown in FIG. 1, a gas sensor unit 1 is disposed in an exhaust passage 2 of an internal combustion engine of a vehicle. An exhaust gas which flows through the exhaust passage 2 is introduced as the measured gas into the gas sensor unit 1. Then, the gas sensor unit 1 measures a NOx concentration in the measured gas with a gas sensor element 100 included in the gas sensor unit 1. Specifically, in addition to the gas sensor element 100, the gas sensor unit 1 is configured to include a sensor housing 101, an insulator 102, element covers 103 and 104, a plurality of sensor harnesses 105, and a sensor control circuit 106. Note that F in FIG. 1 indicates a gas flow direction in which the measured gas flows inside the gas sensor element 100.

The sensor housing 101 holds inside the gas sensor element 100 via the insulator 102. The covers 103 and 104 are fixed to the sensor housing 101. An upstream portion of the gas sensor element 100 is a first element end 100a and a downstream portion of the gas sensor element 100 is a second element end 100b in the exhaust gas flow direction. The second element end 100b faces the sensor control circuit, and the first element end 100a is located opposite to the second element end 100b. The element cover 103 covers an outer periphery side of the first element end 100a. The element cover 103 has a gas introduction hole 103a for introducing, as the measured gas, the exhaust gas from the exhaust pipe into the first element end 100a which is housed inside. The cover 104 covers an outer periphery side of the second element end 100b. The cover 104 has an air introduction hole 104a for introducing atmospheric air into the second element end 100b which is housed inside the gas sensor unit 1. The plurality of sensor harnesses 105 are provided so as to extend over inside and outside the cover 104. The sensor control circuit 106 is connected to the gas sensor element 100 via the plurality of sensor harnesses 105, outside the sensor housing 101 and the element cover 103. The sensor control circuit 106 according to the present embodiment controls voltage supply to a sensor cell 20, a monitor cell 30, and a pump cell 40.

The following describes a detailed configuration of the gas sensor element 100 with reference to FIG. 2. The gas sensor element 100 includes a measurement gas chamber 10, a reference gas chamber 11, the sensor cell 20, the monitor cell 30, the pump cell 40, and a heater 60. The gas sensor element 100 is configured such that the heater 60, and a solid electrolyte body 70 and an insulation layer 90 (described later) are stacked. The measurement gas chamber 10 is formed as a space which is surrounded by the solid electrolyte body 70 and the insulation layer 90. The reference gas chamber 11 is formed as a space which is surrounded by the heater 60 and the solid electrolyte body 70. The following describes components of the gas sensor element 100 in detail.

The measurement gas chamber 10 is a space into which the exhaust gas which is the measured gas is introduced. The measurement gas chamber 10 is formed as a space which is sandwiched between the solid electrolyte body 70 and the insulation layer 90. The insulation layer 90 has a plate shape and is stacked via a first spacer 91 on the solid electrolyte body 70 having a plate shape. When the solid electrolyte body 70 is viewed from the front, the first spacer 91 forms a C-shape, with a part being open, and thus, the measurement gas chamber 10 has a box shape, with a part being open. The one part is an introduction port 10a for the exhaust gas. In the introduction port 10a according to the present embodiment, a diffusion resistance body 93 is disposed and the exhaust gas is introduced from the introduction port 10a into the measurement gas chamber 10 passing through the diffusion resistance body 93. That is, the exhaust gas is introduced into the measurement gas chamber 10 under predetermined diffusion resistance by the diffusion resistance body 93.

As the solid electrolyte body 70 according to the present embodiment, for example, yttria stabilized zirconia (YSZ) can be used. Under a temperature of not less than approximately 600° C., YSZ exerts a function as a solid electrolyte. The solid electrolyte body 70 is heated by the heater 60 (described later) to a temperature of approximately 800° C. so that the function as the solid electrolyte is maintained. As the solid electrolyte body 70, a material such as calcium oxide stabilized zirconia or alumina stabilized zirconia can also be used. As the insulation layer 90 and the first spacer 91, alumina or other commonly known insulation materials can be used.

The reference gas chamber 11 is a space into which a reference gas is introduced. The reference gas is used for generating a reference potential for calculating a concentration of NOx which is the specific gas. As the reference gas, for example, atmospheric air is introduced into the reference gas chamber 11. The reference gas chamber 11 is formed as a space sandwiched between the heater 60 and the solid electrolyte body 70. The solid electrolyte body 70 is stacked via a second spacer 92 on the heater 60 formed in a plate shape. When the solid electrolyte body 70 is viewed from the front, the second spacer 92 is formed on a side closer to the diffusion resistance body 93. In the reference gas chamber 11, an introduction port for the atmospheric air (not shown) is open toward a side opposite to the second spacer 92.

Thus, the solid electrolyte body 70 is formed so as to be located between the measurement gas chamber 10 and the reference gas chamber 11 and is exposed to both of the measurement gas chamber 10 and the reference gas chamber 11. This allows ions to move in the solid electrolyte body 70 in accordance with a difference between a NOx concentration in the exhaust gas and a NOx concentration in the atmospheric air so that a sensor current is generated.

The sensor cell 20 includes a sensor electrode 21, the solid electrolyte body 70, and a reference electrode 80. The sensor electrode 21 is formed on the solid electrolyte body 70 so as to be exposed to the measurement gas chamber 10. Meanwhile, the reference electrode 80 is formed on the solid electrolyte body 70 so as to be exposed to the reference gas chamber 11. That is, the solid electrolyte body 70 is sandwiched between the sensor electrode 21 and the reference electrode 80. According to the present embodiment, the sensor cell 20, the monitor cell 30, and the pump cell 40 share the solid electrolyte body 70 and the reference electrode 80.

The sensor electrode 21 is a noble metal catalyst containing platinum (Pt) and rhodium (Rh). Furthermore, the sensor electrode 21 contains a solid electrolyte which is made of YSZ identical in composition to YSZ of the solid electrolyte body 70. That is, the sensor electrode 21 is an electrode which is made of platinum and rhodium acting as catalysts and the solid electrolyte having ionic conductivity. The solid electrolyte contained in the sensor electrode 21 is integrally combined with the solid electrolyte body 70 constituting the sensor cell 20 so that ionic conduction is possible between the solid electrolyte and the solid electrolyte body 70.

NOx contained in the exhaust gas which has been introduced into the measurement gas chamber 10 is adsorbed to an exposed surface of noble metal and is ionized into nitrogen ions and oxygen ions by catalyst action. Among these, the oxygen ions are conducted in the solid electrolyte constituting the sensor electrode 21. The oxygen ions are further conducted to the solid electrolyte body 70 and is detected as the sensor current. Based on an amount of the sensor current, a concentration of NOx is detected. A detailed configuration of the sensor electrode 21 will be described in detail later.

The monitor cell 30 includes a monitor electrode 31, the solid electrolyte body 70, and the reference electrode 80. As described above, the monitor cell 30 shares the solid electrolyte body 70 and the reference electrode 80 with the sensor cell 20. The monitor electrode 31 is formed on the solid electrolyte body 70 so as to be exposed to the measurement gas chamber 10. The monitor electrode 31 is an electrode containing, for example, platinum (Pt) and gold (Au). Although the monitor electrode 31 is incapable of decomposing NOx, the monitor electrode 31 decomposes oxygen molecules so that an electric current caused by oxygen ions flows.

The monitor electrode 31 is formed next to the sensor electrode 21 in a direction approximately orthogonal to a flow direction of the exhaust gas flowing from the introduction port 10a to the sensor cell 20. That is, the sensor electrode 21 and the monitor electrode 31 are exposed in the same manner to the exhaust gas which is approximately uniformly introduced into the measurement gas chamber 10. The monitor cell 30 detects a concentration of residual oxygen contained in the exhaust gas in which an oxygen concentration has been adjusted by the pump cell 40. Specifically, the monitor cell 30 detects an electric current which is caused by the residual oxygen and flows in the solid electrolyte body 70. By subtracting an electric current which is caused by the oxygen ions and is outputted from the monitor cell 30 from an electric current which is caused by the oxygen ions and is outputted from the sensor cell 20, the gas sensor element 100 is capable of detecting a concentration of NOx by canceling an offset of an electric current caused by the oxygen ions and outputted from the sensor cell 20 which electric current is caused by the residual oxygen.

The pump cell 40 is located on a side closer to the introduction port 10a than the sensor cell 20 and the monitor cell 30 are. The pump cell 40 includes a pump electrode 41, the solid electrolyte body 70, and the reference electrode 80. The pump electrode 41 is formed on the solid electrolyte body 70 so as to be exposed to the measurement gas chamber 10. The pump electrode 41 is an electrode containing platinum (Pt) and gold (Au) as with the monitor electrode 31. The pump electrode 41 reduces oxygen so that oxygen ions are generated. The oxygen ions are conducted in the solid electrolyte body 70 to move to the reference electrode 80 side and is discharged into the reference gas chamber 11. Thus, the pump cell 40 is a cell which adjusts the oxygen concentration in the measurement gas chamber 10 by its pumping action. That is, on the introduction port 10a side with respect to the flow of the exhaust gas, the pump cell 40 adjusts the oxygen concentration in the exhaust gas. With respect to the exhaust gas in which the oxygen concentration has been adjusted, the sensor cell 20 and the monitor cell 30 output an electric current caused by NOx and an electric current caused by the residual oxygen, respectively.

In addition, the pump cell 40 according to the present embodiment has a function of decomposing a substance contained in the exhaust gas so that a reducing gas is generated. Specifically, the pump cell 40 decomposes water molecules contained in the exhaust gas so that hydrogen gas which is reducing is generated. When the gas sensor element 100 is activated, oxygen occluded in the sensor electrode 21 is reduced and removed by the hydrogen gas.

The heater 60 maintains a temperature of the solid electrolyte body 70 at not less than approximately 600° C. so that YSZ functions as the solid electrolyte. The heater 60 is formed such that a conductor layer 62 which generates heat by energization is provided between ceramics substrates 61. The conductor layer 62 is formed so that when surfaces on which the electrodes 21, 31, 41, and 80 are formed are viewed from the front, the conductor layer 62 overlaps the solid electrolyte body 70 and thus temperatures at least in and near portions in which the electrodes 21, 31, 41, and 80 are formed can be maintained at activation temperatures. Temperature distribution in the solid electrolyte body 70 achieved by the heater 60 needs to be set as appropriate depending on required performance. The arrangement of the conductor layer 62 can be set in accordance with required temperature distribution.

Figure 3:
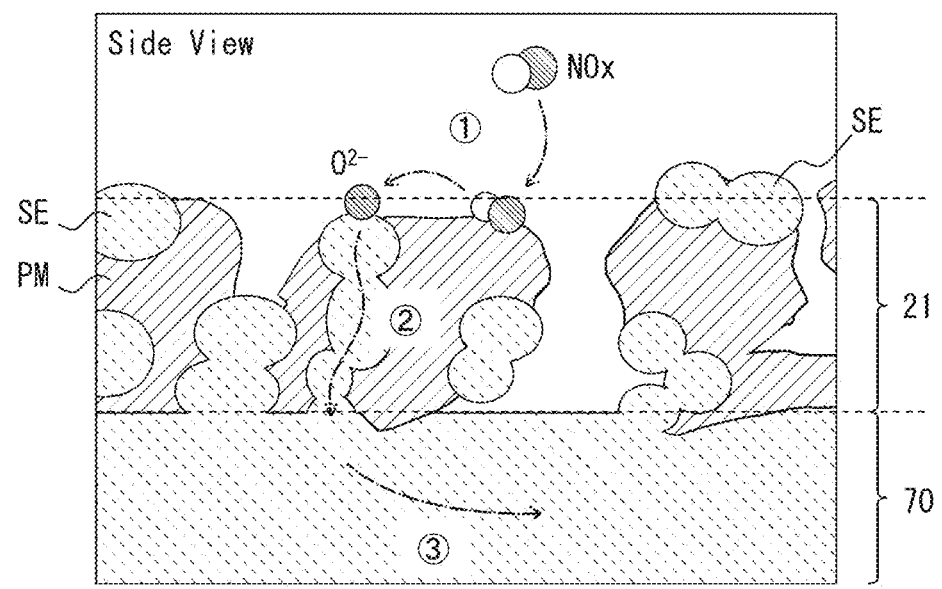
FIG. 3 is a conceptual diagram illustrating a cross-section of a sensor electrode and how reduction occurs.
Figure 4:
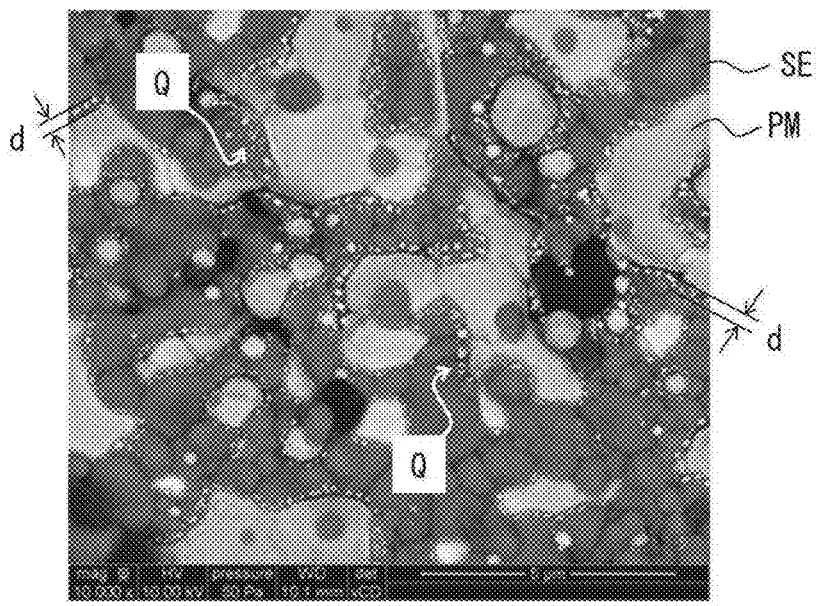
FIG. 4 shows a result of observation of a detailed configuration near the sensor electrode under a scanning electron microscope.

The following describes a detailed configuration of the sensor electrode 21 with reference to FIGS. 3 and 4.

FIG. 3 is a view schematically showing a cross-section of the sensor electrode 21 and the solid electrolyte body 70 which is a substrate of the sensor electrode 21 in the same direction as in the side view shown in FIG. 2. The sensor electrode 21 is formed on the solid electrolyte body 70 so as to be exposed to the measurement gas chamber 10. As described above, the sensor electrode 21 is an electrode which is made of platinum and rhodium acting as the catalysts and the solid electrolyte having ionic conductivity. Specifically, the sensor electrode 21 has noble metal regions PM containing Pt and Rh, and solid electrolyte regions SE. The solid electrolyte regions SE enter gaps between the noble metal regions PM which are scattered, and form a path for ionic conduction. As described above, a main ingredient of the solid electrolyte regions SE according to the present embodiment is YSZ. The solid electrolyte constituting the sensor electrode 21 is integrally merged with the solid electrolyte body 70 as the substrate at an interface between the sensor electrode 21 and the solid electrolyte body 70.

FIG. 4 shows a result of observation, under a scanning electron microscope, of the sensor electrode 21 viewed from the same direction as in the front view shown in FIG. 2. In FIG. 4, regions which are observed to have a light gray color are the noble metal regions PM, and the regions form a plurality of clusters and constitute the sensor electrode 21. Meanwhile, regions which are observed to have a dark gray color are the solid electrolyte regions SE. Portions which are observed to have a black color are spaces containing none of Pt, Rh, and YSZ. Such portions are contained in a certain proportion, as what are referred to as pores, in the sensor electrode 21.

In addition to the above regions, the sensor electrode 21 have mixed regions Q in which the noble metal containing Pt and Rh, and the solid electrolyte are mixed, at interfaces between the noble metal regions PM and the electrolyte regions SE. As observed in FIG. 4, the mixed regions Q are mainly formed along the interfaces between the noble metal regions PM and the electrolyte regions SE. The mixed regions Q have a thickness d which is approximately constant. For example, in FIG. 4, the mixed regions have the thickness d of approximately 0.5 μm as an average or median value.

The following briefly describes, with reference to FIG. 3, a reaction to NOx which is the specific gas in the measured gas. NOx (e.g., nitric oxide) which is present in a vapor phase is adsorbed to the noble metal region PM which is exposed to a surface of the electrode. NOx molecules move on a surface of the noble metal and reached the electrolyte region SE. The mixed region Q is formed at the interface between the noble metal region PM and the electrolyte region SE. In the mixed region Q, a three-phase interface of a noble metal portion, a solid electrolyte portion, and NOx-containing vapor phase is likely to occur. The three-phase interface is a reaction site where a reduction reaction to molecules in the measured gas occurs. At the three-phase interface, the NOx molecules are reduced so that oxygen ion are generated. The oxygen ions reach the solid electrolyte body 70 via the electrolyte region SE, thereby producing a sensor current.

As described above, since the mixed region Q is the reaction site for the reduction reaction, by setting the thickness d of the mixed region Q to be great, it is possible to decrease the reaction resistance for the reaction and the diffusion resistance for ion diffusion which occurs after the reduction. This small reaction and diffusion resistances improve reduction reactivity of the sensor electrode to the measured gas.

The following briefly describes a method for producing the sensor electrode 21. First, YSZ in a paste form containing noble metal powder which has been prepared so that a mass percentage of Rh to a total mass of Pt and Rh is a predetermined value is placed on the solid electrolyte body 70 which is the substrate. Then, the components of the gas sensor element 100 are assembled in an appropriate manner. With respect to the gas sensor element 100 thus assembled, an energization process is performed between the sensor electrode 21 and the reference electrode 80. In this regard, in the sensor electrode 21, a Pt—Rh alloy is dispersed to the solid electrolyte body 70, and the noble metal regions PM, the electrolyte regions SE, the mixed regions Q, and pores are formed. In the reference electrode 80, Pt is dispersed to the solid electrolyte body 70, and pores into which the reference gas (atmospheric air according to the present embodiment) flows are formed.

The thickness d of the mixed region Q depends on a condition related to formation of the sensor electrode 21. The thickness d of the mixed region Q is determined, for example, depending on interrelationships between various parameters for energization at the time of the formation of the electrode, such as voltage, electric current, time, temperature, air pressure, and composition ratio of Pt to Rh.

Figure 5:
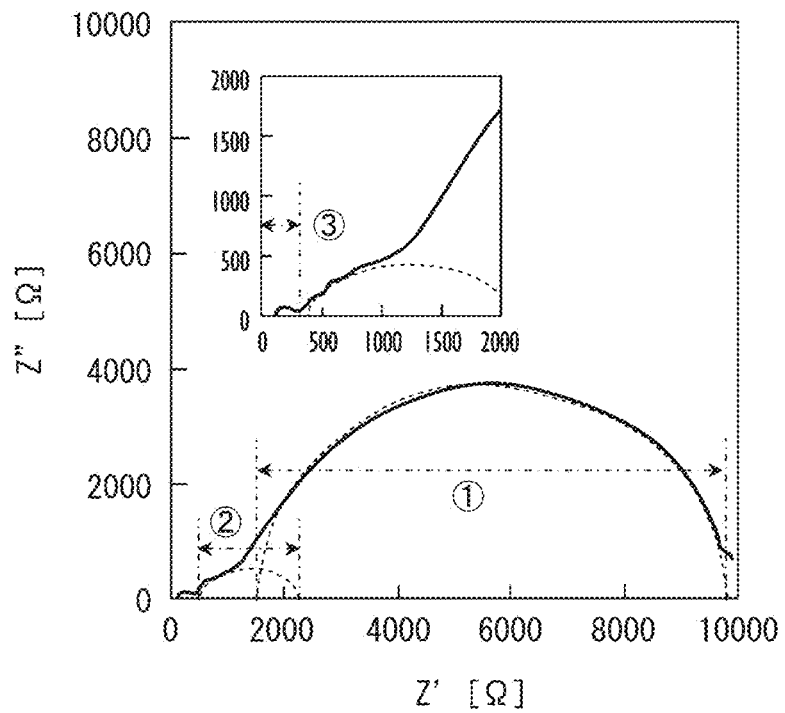
FIG. 5 is a graph showing an example of a Cole-Cole plot for measurement of a reaction resistance.

The following describes the reaction resistance with reference to FIG. 5.

A resistance for the reaction in the sensor electrode 21 related to the detection of the concentration of the specific gas is a sum total of a diffusion/reaction resistance R1 for a reduction reaction of molecules in the measured gas and ion diffusion after the reduction, a charge transfer resistance R2 for ionic conduction in the electrolyte region SE in the sensor electrode 21, and an electrolyte resistance R3 for ionic conduction of the solid electrolyte body which is the substrate. This resistance is herein referred to as reaction resistance R. That is, R R1+R2+R3.

Since the reaction resistance R is expected to include the above plurality of resistance components, the reaction resistance R is measured by a complex impedance analysis method. A method for measuring the reaction resistance R follows a general complex impedance analysis method and is not described here in detail. A Cole-Cole plot as shown in FIG. 5 is obtained by supplying an alternating current voltage between the sensor electrode 21 and the solid electrolyte body 70. FIG. 5 is an example showing a result obtained by the complex impedance analysis method. FIG. 5 shows a result obtained by performing measurement, at a NOx concentration of 2000 ppm, a frequency of 10 mHz to 5 MHz, an amplitude of 20 mV, a DC bias of 0.21 V, and a temperature at the sensor electrode 21 of 800° C., in the sensor electrode 21 which has been produced under a predetermined condition. A solid line in FIG. 5 is a plot of an actual measured value. A semicircular dashed line in FIG. 5 is a plot obtained by decomposing the actual measured value into the resistance components.

According to the gas sensor element 100 of the present embodiment, as described above, the reaction resistance R can be broadly divided into three resistance components, that is, the electrolyte resistance R3, the charge transfer resistance R2, and the diffusion/reaction resistance R1 in ascending order of measured resistance values.

The diffusion/reaction resistance R1 is a resistance value shown when NOx molecules pass through a path "1" shown in FIG. 3 and is also a resistance value corresponding to a number "1" shown in FIG. 5. The diffusion/reaction resistance R1 is a resistance exhibited when a NOx molecule which is the specific gas is adsorbed to the surface of the sensor electrode 21 and diffused. The diffusion/reaction resistance R1 includes, for example, an adsorption resistance of the NOx molecules to the noble metal region PM exposed to the surface of the sensor electrode 21 and a diffusion resistance for diffusion on the noble metal region PM.

The charge transfer resistance R2 is a resistance value shown when oxygen ions pass through a path "2" shown in FIG. 3 and is also a resistance value corresponding to a number "2" shown in FIG. 5. The charge transfer resistance R2 is an electrical resistance exhibited until oxygen ions which are generated by decomposition of the NOx molecules at the three-phase interface of the noble metal region PM, the electrolyte region SE, and the vapor phase is conducted in the electrolyte region SE and reaches the solid electrolyte body 70.

The electrolyte resistance R3 is a resistance value shown when oxygen ions pass through a path "3" shown in FIG. 3 and is also a resistance value corresponding to a number "3" shown in FIG. 5. The electrolyte resistance R3 is composed of an electrolyte grain resistance in the solid electrolyte body 70 which is the substrate, a grain boundary resistance, and an electrical resistance, for example, in a lead wire.

Figure 6:
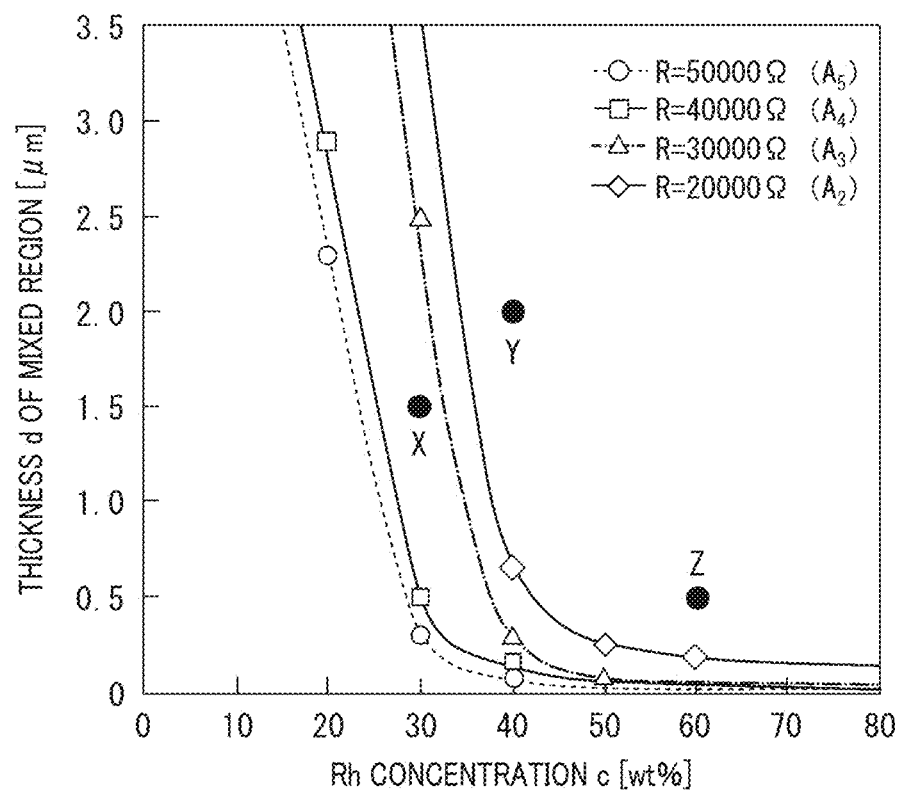
FIG. 6 is a graph showing a correlation between a Rh concentration and a thickness of a mixed region.
Figure 7:
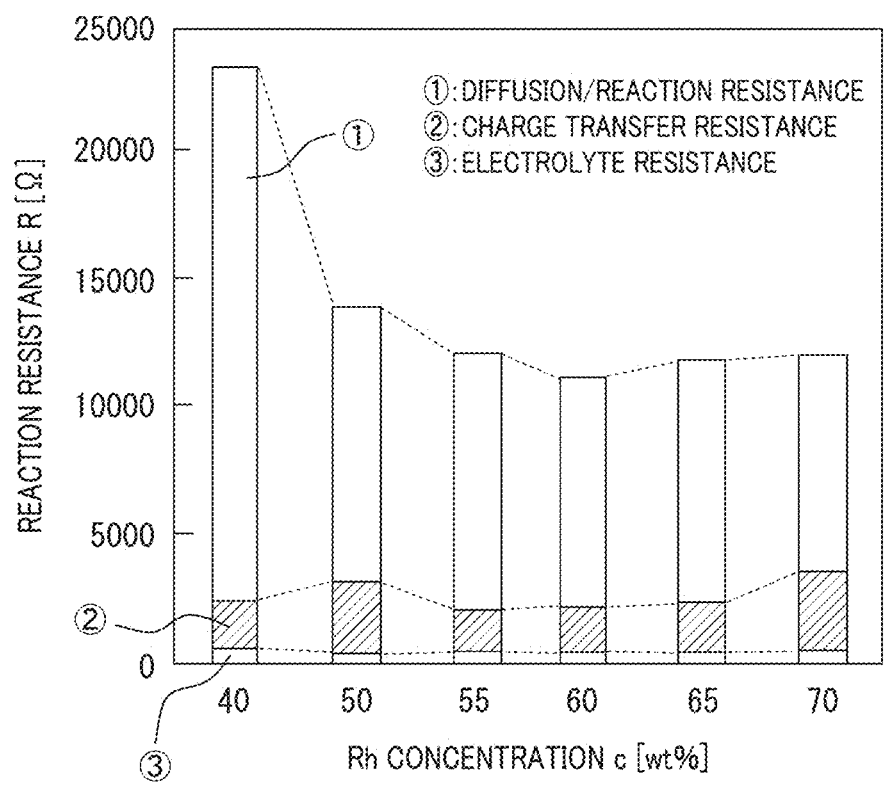
FIG. 7 is a graph showing a relationship between a mass percentage concentration c of Rh and a detail of a reaction resistance R.

The following describes, with reference to FIGS. 6 and 7, suitable conditions for the thickness d of the mixed region Q and a mass percentage concentration c of Rh to the total mass of Pt and Rh in the sensor electrode 21.

As described above, the three-phase interface of the noble metal region PM, the electrolyte region SE, and the vapor phase is a reaction site where a reduction reaction to molecules in the measured gas occurs. Thus, by setting the thickness d of the mixed region Q to be great, it is possible to decrease the reaction resistance R for the reaction. This makes it possible to improve the reduction reactivity of the sensor electrode 21 to the measured gas.

The inventor has found, by a heat endurance test for the sensor electrode 21, a phenomenon of increase in the diffusion/reaction resistance R1 and the charge transfer resistance R2 which is caused by ionic conduction in the solid electrolyte. As one of causes of the phenomenon, the inventor has focused on aggregation of the noble metal in the mixed region Q. As the thickness d of the mixed region Q is greater, the increase in the diffusion/reaction resistance R1 and the charge transfer resistance R2 which is caused by the aggregation of the noble metal while enduring heat becomes more remarkable. That is, although expansion of the thickness d of the mixed region Q decreases the reaction resistance R by the increase in reaction site and this improves the reduction reactivity, the expansion causes a contradictory problem of the increase in reaction resistance caused by heating.

Thus, the inventor has focused on the mass percentage concentration c of Rh and examined a relationship between the thickness d of the mixed region Q and the concentration c. FIG. 6 shows a result obtained by plotting the mass percentage concentration c of Rh on a horizontal axis and the thickness d of the mixed region Q when the reaction resistance R has a predetermined value. From FIG. 6, a clear correlation has been found between the mass percentage concentration c of Rh and the thickness d of the mixed region Q for obtaining a predetermined reaction resistance R. That is, in a c-d orthogonal coordinate system which is defined by the mass percentage concentration c of Rh (Rh concentration c) and the thickness d of the mixed region Q, it is possible to define a correlation curve A which represents a correlation between the concentration c and the thickness d when the reaction resistance R to the measured gas is constant.

FIG. 6 is a plot of a correlation curve $A_2$ when the reaction resistance R=20 kΩ, a correlation curve $A_3$ when the reaction resistance R=30 kΩ, a correlation curve $A_4$ when the reaction resistance R=40 kΩ, and a correlation curve $A_5$ when the reaction resistance R=50 kΩ. With the same reaction resistance, a smaller thickness of the mixed region Q tends to be achievable as the Rh concentration c is increased. In the c-d orthogonal coordinate system, the correlation curve A is a curve in which the thickness d of the mixed region asymptotically approaches zero as the mass percentage concentration c increases. The correlation curve A for each reaction resistance R in FIG. 6 is shown as a function which has been fitted from data on three sets of coordinates. A function which is suitable for the fitting includes, for example, a first exponential function ($d=d_0+K_1\exp[-(c-c_0)/K_2]$; $d_0$, $c_0$, $K_1$, and $K_2$ are each a constant), a second exponential function, and a third exponential function.

As shown in FIG. 6, a correlation curve for a given reaction resistance is plotted such that the Rh concentration c has a positive coordinate point and the thickness d of the mixed region has a positive coordinate point as compared with a correlation curve for a reaction resistance lower than the given reaction resistance. That is, it is suggested that the sensor electrode 21 is configured to allow the reaction resistance R to be decreased as the mass percentage concentration c of Rh has a more positive coordinate point and the thickness d of the mixed region has a more positive coordinate point. For example, when the thickness of the mixed region Q is required to be 1.5 μm, it can be determined with reference to FIG. 6 that by setting the concentration c of Rh to be not less than approximately 25%, it is possible to cause the reaction resistance R for the reaction of the specific gas NOx to be not more than 40 kΩ. For example, when the concentration c and the thickness d in the sensor electrode 21 is set so that c=30 wt % and d=1.5 μm (coordinates X in FIG. 6), it is possible to cause the reaction resistance R to be not more than 40 kΩ. Furthermore, for example, when the concentration c and the thickness d in the sensor electrode 21 is set so that c=40 wt % and d=2.0 μm (coordinates Y in FIG. 6), it is possible to cause the reaction resistance R to be not more than 20 kΩ. When the thickness d of the mixed region Q is requested so that d=0.5 μm, which is a smaller value, for example, by setting the concentration c in the sensor electrode 21 so that c=60 wt % (coordinates Z in FIG. 6), it is possible to decrease the thickness d as compared with the condition for the coordinates Y, while maintaining the setting of the reaction resistance at not more than 20 kΩ. When the thickness d of the mixed region Q can be set to be small, it is possible to reduce the increase in the reaction resistance R caused by heating.

The inventor has also examined dependency of the reaction resistance R on the Rh concentration. FIG. 7 shows a result obtained by examining a breakdown of the reaction resistance R in a sample in which the mass percentage concentration c of Rh has a predetermined to value when the thickness d of the mixed region Q is constant. According to FIG. 7, in the sample which achieves a reaction resistance of approximately 23 kΩ at the Rh concentration of 40 wt %, when the Rh concentration is set to be not less than 60 wt %, the reaction resistance is approximately constant at approximately 11 kΩ. When the Rh concentration is set to be 70 wt %, the charge transfer resistance R2 tends to be increased as compared with a lower concentration level of less than 65 wt %. That is, it is suggested that when the Rh concentration is set to be greater than 70 wt %, the reaction resistance R is increased as the charge transfer resistance R2 is increased.

The increase in the charge transfer resistance R2 is surmised to be caused by separation of the sensor electrode 21 from the solid electrolyte body 70 due to a heating and cooling cycle. The result indicates that the mass percentage concentration c of Rh to the total mass of Pt and Rh is preferably not more than 70 wt %. This set mass percentage concentration c of Rh maintains the reduction reactivity to the specific gas without increasing the reaction resistance R by heat load caused by the heating and cooling cycle.

Since Rh is reductive, Rh has a property of being stable by aggregation. The inventor has performed an experiment in which heat load caused by maintaining a high temperature is applied to the sensor electrode 21. The inventor then has found that Rh atoms are aggregated in the mixed region R and transit to the noble metal region PM. From this result, it is surmised that it is impossible to set the thickness d of the mixed region Q to be greater than 3 μm. In other words, the sensor electrode 21 is preferably designed such that the thickness d of the mixed region Q is set to be not more than 3 μm. This set thickness d of the mixed region Q maintains the reduction reactivity of the sensor electrode 21 to the specific gas without increasing the reaction resistance R by heat load caused by maintaining a high temperature.

Other Embodiments

Although in the aforementioned embodiment, the gas sensor element 100 including the monitor cell 30 has been described, the monitor cell 30 is not an essential component in terms of detecting a concentration of the specific gas in the measured gas. Note, however, that the gas sensor element 100 including the monitor cell 30 is preferable in terms of accurately detecting an oxygen concentration in the gas in which the oxygen concentration has been adjusted by the pump cell 40, and correcting background for an electric current which is caused by oxygen ions and is outputted from the sensor cell 20.

Furthermore, although in the aforementioned embodiment, the noble metal containing Pt and Rh has been described as the noble metal constituting the sensor electrode 21, palladium (Pd) or ruthenium (Ru) can be added to Pt and Rh.

Figure 8:
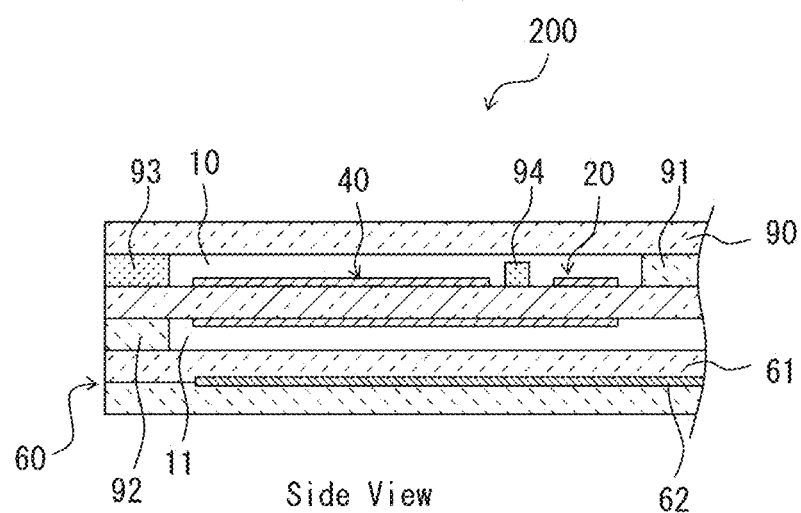
FIG. 8 is a cross-sectional view showing a detailed configuration of a gas sensor element according to anther embodiment.

The measurement gas chamber 10 can be configured such that a space in which the sensor cell 20 is formed and a space in which the pump cell 40 is formed are separated from each other so that the measured gas is movable between these spaces. Specifically, for example, in the gas sensor element 200 shown in FIG. 8, a diffusion rate determining body 94 is formed between the space in which the sensor cell 20 is formed and the space in which the pump cell 40 is formed. The diffusion rate determining body 94 divides the sensor cell 20 from the pump cell 40 to partition the space of the measurement gas chamber 10. In this case, while adjusting diffusion resistance, the diffusion rate determining body 94 allows the measured gas to pass through.

The invention claimed is:

1. A gas sensor element comprising:
a measurement gas chamber into which a measured gas is introduced;
a solid electrolyte body which is disposed in the measurement gas chamber and which has oxygen ion conductivity; and
a sensor electrode which is formed on a substrate constituted by the solid electrolyte body and is for detecting a concentration of a specific gas in the measured gas, wherein:
the sensor electrode contains a noble metal which includes at least rhodium and platinum, contains a solid electrolyte which is identical in quality to the solid electrolyte body of the substrate, has a noble metal region which is formed by the noble metal, has an electrolyte region which is formed by the solid electrolyte, and has a mixed region in which the noble metal and the solid electrolyte are mixed;
the sensor electrode has a predetermined value of reaction resistance;
the platinum and rhodium have a predetermined total mass in the noble metal;
the rhodium in the noble metal has a predetermined first value of a mass percentage concentration to the predetermined total mass of the platinum and rhodium in the noble metal;
the mixed region has a predetermined second value of thickness thereof; and
the predetermined first value of the mass percentage concentration and the predetermined second value of the thickness are larger than a predetermined correlation that is defined between the mass percentage concentration and the thickness while the reaction resistance of the sensor electrode is fixed to a constant of 40 kΩ, whereby the predetermined value of the reaction resistance of the sensor electrode is equal to or smaller than 40 kΩ.

2. The gas sensor element as set forth in claim 1, wherein the predetermined correlation is a curve which has been fitted by using at least three sets of coordinates each of which is a combination of the mass percentage concentration and the thickness of the mixed region.

3. The gas sensor element as set forth in claim 1, wherein the mass percentage concentration of rhodium and the thickness of the mixed region in the sensor electrode have values greater than the predetermined correlation when the reaction resistance of the sensor electrode is 20 kΩ.

4. The gas sensor element as set forth in claim 1, wherein the mass percentage concentration is not more than 70 wt %.

5. The gas sensor element as set forth in claim 1, wherein the thickness of the mixed region is not more than 3 μm.

6. A gas sensor unit comprising:
the gas sensor element recited in claim 1;
a sensor housing which holds the gas sensor element inside;
an element cover which is fixed to the sensor housing to cover a first element end of the gas sensor element and introduces the measured gas into the first element end, the first element end facing a flow of the measured gas; and
a sensor control circuit which controls a voltage applied to the sensor electrode.

7. A method of manufacturing a gas sensor element comprising:
determining a correlation between (a) a mass percentage concentration of rhodium to a total mass of platinum and rhodium in the noble metal and (b) a thickness of the mixed region so that the thickness of the mixed region asymptotically approaches zero as the mass percentage concentration increases for each given reaction resistance;
manufacturing the gas sensor element to include a measurement gas chamber into which a measured gas is introduced;

a solid electrolyte body which is disposed in the measurement gas chamber and which has oxygen ion conductivity; and a sensor electrode which is formed on a substrate constituted by the solid electrolyte body and is for detecting a concentration of a specific gas in the measured gas, wherein:

the sensor electrode contains a noble metal which includes at least rhodium and platinum, contains a solid electrolyte which is identical in quality to the solid electrolyte body of the substrate, has a noble metal region which is formed by the noble metal, has an electrolyte region which is formed by the solid electrolyte, and has a mixed region in which the noble metal and the solid electrolyte are mixed; and the sensor electrode has a predetermined value of reaction resistance;

the platinum and rhodium have a predetermined total mass in the noble metal;

the rhodium in the noble metal has a predetermined first value of a mass percentage concentration to the predetermined total mass of the platinum and rhodium in the noble metal;

the mixed region has a predetermined second value of thickness thereof; and the predetermined first value of the mass percentage concentration and the predetermined second value of the thickness are larger than a predetermined correlation that is defined between the mass percentage concentration and the thickness while the reaction resistance of the sensor electrode is fixed to a constant of 40 kΩ, whereby the predetermined value of the reaction resistance of the sensor electrode is equal to or smaller than 40 kΩ.

8. The gas sensor element as set forth in claim 1, wherein the predetermined first value of the mass percentage concentration and the predetermined second value of the thickness are present in a region which is defined by:

(A) a first line representing the predetermined correlation between the mass percentage concentration and the thickness upon the reaction resistance of the sensor electrode being fixed to the constant of 40 kΩ, (B) a second line corresponding to a straight line which represents the mass percentage concentration being fixed to 70 wt %, and (C) a third line corresponding to a straight line which represents the thickness being fixed to 3 μm.

9. The gas sensor element as set forth in claim 1, wherein the predetermined first value of the mass percentage concentration is equal or larger than 30 wt % and is equal or smaller than 70 wt %, the predetermined second value of the thickness is equal or larger than 1.5 μm and is equal or smaller than 3.0 μm, and the reaction resistance of the sensor electrode is equal or lower than 40 kΩ.

10. The gas sensor element set forth in claim 9, wherein the predetermined first value of the mass percentage concentration is equal or larger than 40 wt % and is equal or lower than 70 wt %, the predetermined second value of the thickness is equal or larger than 2.0 μm and is equal or lower than 3.0 μm, and the reaction resistance of the sensor electrode is equal or lower than 20 kΩ.

11. The gas sensor element set forth in claim 1, wherein the predetermined first value of the mass percentage concentration is equal or larger than 60 wt % and is equal or lower than 70 wt %, the predetermined second value of the thickness is equal or larger than 0.5 μm and is equal or lower than 3.0 μm, and the reaction resistance of the sensor electrode is equal or lower than 20 kΩ.

12. A method of manufacturing a gas sensor element comprising:

preparing a substrate made of a first solid electrolyte body, the substrate having opposing first and second surfaces;

preparing a noble metal powder having a predetermined first value of a mass percentage concentration of rhodium to a total mass of platinum and rhodium;

mixing the noble metal powder into a second solid electrolyte body;

placing the second solid electrolyte body in which the noble metal powder has been mixed on the first surface of the substrate to thereby constitute a sensor electrode on the first surface of the substrate;

placing a reference electrode on the second surface of the substrate;

performing an energizing process between the sensor electrode and the reference electrode to thereby form a noble metal region, an electrolyte region, and a mixed region of noble metal and solid electrolyte in the sensor electrode to thereby cause:

the mixed region to have a predetermined second value of thickness thereof; and the predetermined first value of the mass percentage concentration and the predetermined second value of the thickness to be larger than a predetermined correlation that is defined between the mass percentage concentration and the thickness while the reaction resistance of the sensor electrode is fixed to a constant of 40 kΩ, so that the sensor electrode has a predetermined value of reaction resistance equal to or lower than 40 kΩ.

* * * * *